United States Patent [19]

Wolf-Watz et al.

[11] Patent Number: 5,284,653
[45] Date of Patent: Feb. 8, 1994

[54] FISH VACCINE COMPRISING AN AVIRULENT, INVASIVE BACTERIUM

[75] Inventors: Hans Wolf-Watz; Anders Norquist, both of Umeå; Åke Hagström, Hörnefors, all of Sweden

[73] Assignee: Symbicom Aktiebolag, Umeå, Sweden

[21] Appl. No.: 601,688

[22] PCT Filed: Apr. 6, 1989

[86] PCT No.: PCT/DK89/00075
§ 371 Date: Oct. 31, 1990
§ 102(e) Date: Oct. 31, 1990

[87] PCT Pub. No.: WO89/09616
PCT Pub. Date: Oct. 19, 1989

[30] Foreign Application Priority Data

Apr. 7, 1988 [DK] Denmark .................. 1897/88

[51] Int. Cl.$^5$ ................. A61K 39/02; C12P 21/06; C12N 1/21
[52] U.S. Cl. ..................... 424/92; 435/69.1; 435/252.3
[58] Field of Search .......... 424/92, 93; 435/69.1, 435/172.1, 252.3, 252.34, 252.8, 253.4

[56] References Cited

U.S. PATENT DOCUMENTS 4,479,936 10/1984 Vandenburgh et al. .......... 424/93

FOREIGN PATENT DOCUMENTS

WO82/02491 8/1982 PCT Int'l Appl. ........ A61K 39/02
2170708A 8/1986 United Kingdom ........ A61K 39/02

OTHER PUBLICATIONS

Trust et al Inf & Imm 34:782-787 1981.
Belas et al J of Bact. 158:890-896 1984.
Tolmasky et al J of Bact 160:860-866 1984.
Donald F. Amend, "Current Status and Future Needs of Vibrio Anguillarum bacterins", *Develop. Biol. Standard*, 49:403-417 (1981).
Agius et al., "Immunisation of Rainbow Trout, *Salmo gairdneri* Richardson, Against Virbiosis . . . " *J. Fish Dis.* 6:129-134 (1983).
Braaten et al., "Protection of Steelhorn Trout . . . ", *J. Fish Res. Board Can.*, 33:845-847 (1976).
Voon-Loong Chan et al., "In Vitro Generation of Specific Deletions in DNA cloned in M13 Vecors" *Nucleic Acids Research*, 12(5):2407-2419 (1984).
Cipriano et al., "Immunization of Salmonids against the fish pathogen, *Aeromonas salmonicida*", *Nat. Fish Hlth. Lab.*, 14:201-211 (1983).
Cipriano et al., "Immersion and Injection Vaccination of Salmonids Against Furunculosis . . . ", *Prog. Fish-Cult*, 44(4):167-169 (1982).
Jorge H. Crosa, "Molecular Studies", *Bacterial and Viral Diseases of Fish*.
Crosa, *Infect. Immun.*, 27:897-902 (1980).
Crosa, "A Plasmid Associated with Virulence in the Marine Fish Pathogen *Vibrio Anguillerum* Specifies an Iron-sequestering System", *Nature*, 284:566-568 (1980).
Ely, B., 1985,, "Vectors for Transposon Mutagenesis of Non-enteric Bacteria", *Mol. Gen. Genet.* 200, pp. 302-304.
Formal, et al., "Construction of a Potential Bivalent Vaccine Strain: Introduction of *Shigella sonnei* Form 1 Antigen . . . ", *Infect. Immun.*, 34(3):746-750 (1981).
Forsberg, et al., "The Virulence Protein Yop5 of *Yersinia pseudotuberculosis* is regulated . . . ", *Molec. Microbiol.* 2(1):121-133 (1988).

(List continued on next page.)

Primary Examiner—Christine M. Nucker
Assistant Examiner—H. Sidberry
Attorney, Agent, or Firm—Foley & Lardner

[57] ABSTRACT

A live vaccine comprising an avirulent, invasive and immunogenic strain of a fish pathogenic bacterial species is used for immunization of fish against infectious diseases caused by fish pathogens by immersion of the fish into a suspension of the vaccine strain. Suitable strains for the preparation of said vaccine include *Vibrio anguillarum* strains DSM 4506, DSM 4507 and DSM 4508.

31 Claims, 2 Drawing Sheets

OTHER PUBLICATIONS

Hone, D. R. et al, 1987, "Construction of Defined gal E Mutant of Salmonella for use as Vaccines", *J. Inf. Dis.* 156, pp. 167–174.

Inamura, H. et al, 1984, "Toxicity of Extracellular Products of *Vibrio anguillarym*", *Fish Pathol.*, 19 pp. 89–96.

Inamura, H. et al, 1985, "An Extracellular Protease Produced by *Vibrio anguillarym*", *Bull. Jap Soc. Sci. Fish.* 51, pp. 1915–1920.

Ishiguro, et al, "Loss of Virulence During Culture of *Aeronmonas salmonicida* at High Temperature", *J. Bacteriol.*, 148(1):333–340 (1981).

Kawano, K. et al, 1984, "Duration of Protection Against bvibriosis in ayu, *Plecoglossus altivelis*, Vaccinated by Immersion . . . ", *Bull. Jpn. Soc. Sci. Fish.* 50, pp. 771–774.

W. W. Kay, et al., "Purification and Disposition of a Surface Protein Associated with Virulence of *Aeromonas salmonicida*", *J. Bacteriol.*, 147(3):1077–1084 (1981).

Kodama, H. et al, 1984, "Extracellular Virulence Factors of Fish Vibrio:Relationships Between Toxic Material, Haemolysin . . . ", *Am. J. Vet. Res.* 45, pp. 2203–2207.

Maniatis, T. et al, 1982, "Molecular Cloning. A Laboratory Manual", Cold Spring Harbor, New York.

Munn, C. B. 1978, "Haemolysin production by *Vibrio anguillarum*", *FEMS Microbiol. Lett.* 3, pp. 265–268.

Neidhardt, P. C. et al., 1974, "Culture Medium for Enterobacteria", *J. Bacteriol.* 119, pp. 736–747.

Norqvist et al., "Protection of Rainbow Trout against Vibriosis and Furunculosis . . . ", *Appl. Environ. Microbiol.* 55(6):1400–1405 (1988).

Olivier et al., "Immunogenicity of vaccines from a virulent and an avirulent strain of *Aeromonas salmonicida*", *Journal of Fish Diseases* 8:43–55 (1985).

Reed, L. J. et al., 1983, "A Simple Method on Estimating Fifty Per Cent Endpoints", *Am. J. Hyg.*, 27:493–497 (1938).

A. G. Rodina, "Methods of Studying Microorganisms of Nitrogen Cycle", *Meth. in Aquatic Microbiol.* 7-25-1-257.

Edwin Southern, "Gel Electrophoresis of Restriction Fragments", *Methods in Enzymology*, 68:152–176 (1979).

Tebbit et al., "Developments in Biological Standardization, Int. Symposium on Fish Biologics", Serodiagnostics and Vaccines, Heunessen & Anderson, 49:395–402 (1981).

Trust, T. J. et al., 1981, "Serum Resistance and Haemagglutination Ability of Marine Vibrios Pathogenic to Fish", *Immun*, 34, pp. 702–707.

Wahden, M. H. et al., 1982, "A Controlled Field Trial of Live *Salmonella typhy* Strain Ty 21a Oral Vaccine Against Typhoid: Three-year Results", *J. Inf. Dis.* 145, pp. 292–295.

Walter, M. A. et al., 1983, "Iton Uptake System Mediated by *Vibrio anguillarym*, plasmid pJM1", *J. Bacteriol.* 156, pp. 880–887.

Ward, P. D. et al., 1985, "Factors Influencing the Efficacy of Vaccines Against vibriosis Caused by *Vibrio anguillarum*", In Fish Immunology, M. J. Manning and M. F. Tatner (eds.), pp. 221–229.

Winter, et al., "Genetic dissection of tyrosyl-tRNA synthetase", *Biochem. Society Transactions*, 12:224–225 (1984).

Winter, et al., "Redesigning enzyme structure by site-directed mutagenesis: tyrosyl tRNA synthetase and ATP binding", *Nature*, 299:756–758 (1982).

Wolf, M. K. et al., 1986, "Evidence for the Role of a Siderophore in Promoting *Vibrio anguillarum* Infections." *J. Gen. Microbiol*, 132, pp. 2949–2952.

Zoller, et al., "Oligonucleotide–directed mutagenesis using M13–derived vectors . . . ", *Nucleic Acids Research* 10(20):6487–6500 (1982).

FISH VACCINE COMPRISING AN AVIRULENT, INVASIVE BACTERIUM

FIELD OF INVENTION

The present invention relates to a live vaccine for the immunization of fish, a bacterium useful for the vaccine, a method of immunizing fish by means of the bacterium and fish immunized by the vaccine.

TECHNICAL BACKGROUND

Infections occurring among cultured fish, principally salmonid fish, are a major source of economic loss in the fish rearing industry all over the world. It has hitherto been attempted to reduce or eliminate losses resulting from certain infections of bacterial etiology (e.g. furunculosis caused by *Aeromonas salmonicida*, enteric redmouth caused by *Yersinia ruckerii* and vibriosis caused by *Vibrio anguillarum*) by means of chemotherapeutic agents such as sulfa drugs or oxytetracycline. The use of antibacterial agents, however, is rather expensive and, furthermore, drug resistant strains of the various pathogenic bacteria have been known to develop. Besides, the use of antibacterial agents offers no protection against diseases of a viral etiology.

Efforts have therefore been made to develop a vaccine against selected fish pathogens. Thus, a vaccine has been developed against Y. ruckerii (Tebbit et al. in: Developments in Biological Standardization, Vol. 49, International Symposium on Fish Biologics: Serodiagnostics and Vaccines, W. Heunessen and D. P. Anderson (eds.), 1981, pp. 395-402), and *V. anguillarum* (Amend and Johnson in: Developments in Biological Standardization, Vol. 49, International Symposium on Fish Biologics: Serodiagnostics and Vaccines, W. Heunessen and D. P. Anderson (eds.), 1981, pp. 403-418; Agius et al., *J. Fish Dis.* 6, 1983, pp. 129-134). These vaccines are based on formalin-killed virulent bacteria. The efficacy of these vaccines has been tested and it has been shown that the route of administration of the vaccines plays an important part for the strength of the resulting immune response (Kawano et al., *Bull. Jpn. Soc. Sci. Fish.* 50, 1984, pp. 771-774; Ward et al., in *Fish Immunology*, M. J. Manning and M. F. Tatner (eds.), 1985, pp. 221-229). Experiments have shown that injection of a vaccine preparation gives by far the best result with the longest duration of the immunization, while immersion and oral administration give a less efficient protection against the infections in question.

Further, a vaccine comprising chloroform-inactivated whole cells, soluble antigen and combined whole cell and soluble antigen of an avirulent strain of *Aeromonas salmonicida* has been shown to protect fish against furunculosis (Cipriano et al., *J. World Maricul. Soc.*, 1983, 14, 201-211).

An improved understanding of the pathogenic properties of the fish pathogens against which it is desired to develop a useful immune response is important for the construction of an efficient vaccine. In spite of the widespread occurrence of epizootics in fish farms caused by a variety of different pathogens, both bacterial and viral, studies of the properties contributing to virulence have so far been limited in number. In the case of V. anguillarum, a number of studies have established the existence in this bacterium of a virulence plasmid of 65 kb (kilobase pairs) which encodes a complex system important to the ability of the bacterium to take up $Fe^{3+}$ (Crosa, Nature 284, 1980, pp. 566-568). It has been shown for many pathogenic microorganisms that the ability to take up $Fe^{3+}$ is important for the bacteria during the process of infection. If V. anguillarum is cured of the virulence plasmid, it becomes avirulent for fish (Crosa et al., *Infect. Immun.* 27, 1980, pp. 897-902).

Furthermore, a number of publications describe possible virulence determinants such as serum resistance (Trust et al., *Infect. Immun.* 34, 1981, pp. 702-707), hemolysin (Munn, *FEMS Micribiol. Lett.* 3, 1978, pp. 265-268), extracellular protease (Inamura et al., *Bull. Jap. Soc. Sci. Fish.* 51, 1985, pp. 1915-1920) and other extracellular factors (Kodama et al., *Am. J. Vet. Res.* 45, 1984, pp. 2203-2207). It has been possible in one way or another to correlate these virulence determinants to the outbreak of disease. However, it has not yet been conclusively proved that these bacterial products are virulence determinants which are important for the pathogenicity of the bacterium.

In recent years, interest has increased in developing live vaccines based on live attenuated bacterial strains for use in the prevention of human diseases, in particular against enteric agents (Hone et al., *J. Inf. Dis.* 156, 1987, pp. 167-174; Wahdan et al., *J. Inf. Dis.* 145, 1982, pp. 292-295). Cipriano and Stasliper, *Prog. Fish-Cult.*, 44, 1982, 167-169, have disclosed a vaccine comprising an attenuated *A. salmonicida* strain. Live vaccines generally have the advantage over vaccines based on killed pathogens or bacterial components that they confer a higher degree of immunity as well as a more prolonged effect, and is more complete than when single components such as antigens are administered. Furthermore, they may require a smaller efficacious dosage than killed pathogens or single components. Live vaccines may also be less expensive to produce than those based on a purified single component, no purification step being required. It would therefore be an advantage to develop a live vaccine for administration to fish requiring a lower immunization dosage than existing fish vaccines based on killed pathogens or membrane components.

A need clearly exists to develop a vaccine against fish pathogens which can provoke a long-lasting and efficient immunological protection against a broad spectrum of fish pathogens after immersion of the fish into the vaccine. Ideally, such a vaccine should comprise a bacterial strain which possesses as many characteristics of the pathogenic microorganisms as possible, but without their ability to cause disease. It is of special significance to select vaccine strains which can penetrate into and proliferate in the fish body, thereby eliciting a strong immune response.

SUMMARY OF THE INVENTION

Accordingly, the present invention relates to a live vaccine for the immunization of fish against diseases caused by fish pathogens, the vaccine comprising an avirulent, invasive, immunogenic mutant strain of a fish pathogenic bacterium.

The term "pathogenic" denotes the ability of a microorganism to cause disease. Pathogenicity is a taxonomically significant attribute, being the property of a species; thus, e.g. the bacterial species *Vibrio anguillarum* is said to be pathogenic for fish. The individual strain of a bacterial species may, however, vary widely in their ability to harm the host species, and this relative pathogenicity is termed "virulence". Accordingly, virulence is an attribute of a strain, not a species; one may speak of a highly virulent, a weekly virulent, or even an avirulent strain of a particular microbial species, e.g. *Vibrio anguillarum*. In general, the virulence of a strain of a pathogenic species is determined by two factors: its "invasiveness", or ability to penetrate into and proliferate in the body of the host, and its "toxigenicity", or ability to produce chemical substances that damage the tissues of the host. A virulent strain of a bacterial species may lose its virulence, but still maintain its ability to invade the host but without causing disease.

In this context, the term "avirulent" is understood to mean that an originally virulent bacterial strain has lost its ability to cause disease in fish infected with the strain, although its ability to invade fish, i.e. to penetrate into the fish by the usual route of the bacteria and to proliferate in the body of the fish, remains substantially intact, it being a decided advantage that the bacteria are able to penetrate by themselves into the fish in order to provoke a relevant immune response there instead of having to rely on extraneous methods such as injection (this being a too costly, though efficient, administration route where fish are concerned) to arrive at a site in the fish where their presence will produce a relevant immune response. Avirulent mutants of the pathogenic bacteria may be selected by subjecting fish to experimental infections by immersion in a suspension contaminated with each mutant strain and determining the $LD_{50}$ (the dosage required to kill 50% of the fish in the bath), for instance as described in detail in Example 1 below. A mutant strain with an $LD_{50}$ exceeding by immersion $2 \times 10^7$ bacteria/ml is defined as avirulent in the context of the present invention. However, for other strains useful in the live vaccine of the invention, the $LD_{50}$ may be lower, the strains being considered to be avirulent even so.

The degree of virulence of a particular bacterial strain may also depend on the susceptibility of different fish species to the bacteria.

In the present context, the term "mutant strain" is defined as a strain which has been isolated as a spontaneous mutant (a frequent phenomenon in nature) or in which a mutation has been deliberately induced by subjecting a parent bacterial strain to treatment with a mutagen such as ultraviolet radiation, ionizing radiation, or a chemical mutagen such as mitomycin C, 5-bromouracil, methylmethane sulphonate, nitrogen mustard, or a nitrofuran, or by applying recombinant DNA techniques.

The term "immunogenic" is understood to mean that the strain is capable of provoking a relevant immune response in the fish to which the vaccine has been administered. There is evidence to suggest that live attenuated strains may in fact provoke a stronger immune reaction than killed pathogens as the antigenic determinants of a live strain are not impaired by chemical treatment. Preferred strains of the invention are such that confer immunity against both homologous and heterologous strains of the same pathogen, i.e. both the parent strain from which the mutant is derived and other pathogenic strains of the same species, in order to afford a broad-spectrum protection against the pathogen in question. It has even been established (cf. Example 2 of the present specification) that certain mutant strains may give rise to cross-protection against another bacterial species than that to which the mutant strain belongs without any DNA from the other species coding for an antigenic determinant thereof having deliberately been inserted into the mutant. There is also some indication (cf. Example 1 of the present specification) that mutants selected or deliberately induced from virulent strains able to infect fish by immersion show a particularly high protection by the immersed vaccination, the reason possibly being that the high virulence of the parent strain reflects a high degree of invasiveness which property is retained in the mutant derived therefrom.

In another aspect, the present invention relates to an avirulent, invasive mutant strain of a fish pathogenic bacterium for use as a live vaccine for the immunization of fish against diseases caused by fish pathogens.

In a further aspect, the invention relates to the use of such a live avirulent, invasive mutant strain for the preparation of a live vaccine for the immunization of fish against diseases caused by fish pathogens, as well as a method of immunizing fish against diseases caused by fish pathogens which comprises administering to the fish an immunogenically effective amount of a live avirulent, invasive mutant strain of a fish pathogenic bacterium.

In a still further aspect, the invention relates to a fish which has been immunized with the live vaccine of the invention. This will generally belong to one of the fish species reared for commercial purposes, principally salmonid fish which have so far been of the greatest commercial importance, such as various species of the genera Salmo, Salvelinus and Oncorhynchus, but also eel, catfish, carp and ayu (commercially reared in Japan).

DETAILED DISCLOSURE OF THE INVENTION

Apart from being isolated as a spontaneous mutant of a pathogenic bacterium or produced by treating a virulent pathogenic bacterium with a mutagen as indicated above, the avirulent mutant strain may also be produced by curing a virulent strain of a virulence plasmid since this makes the bacterium avirulent for fish, in the case of *V. anguillarum* a 65 kb plasmid; cf. Crosa et al., *Infect. Immun.* 27, 1980, pp. 897-902. Furthermore, the mutant strain may be one in which a gene the product of which is required for bacterial virulence is defective or absent, i.e. a strain produced by recombinant DNA techniques (this includes a defect in a promoter or a regulatory system for the gene). The gene may be one which codes for one of the postulated virulence determinants such as serum resistance, hemolysin, extracellular protease and possibly other extracellular toxic products as indicated above, but may also code for other functions or products of importance to the virulence of the bacteria.

The defect in the gene may be caused by a DNA insertion which makes the reading frame of the gene out of phase. The DNA insertion may be of any length from a single base pair to an entire gene. Shorter insertions may be carried out by site specific mutagenesis by means of synthetic oligonucleotides in a manner known per se, e.g. as described in G. Winter et al., *Nature* 299, 1982, pp. 756-758, or Zoller and Smith, *Nucl. Acids Res.*

10, 1982, pp. 6487-6500. Insertion of larger DNA fragments may be performed by gene block insertions (Forsberg and Wolf-Watz, *Mol. Microbiol.* 2, 1988, pp. 121-137); such insertions may be either in-frame (e.g. antibiotic markers) or out-of-frame. Apart from this, the DNA insertion may be in the form of a transposon insertion. A transposon may be introduced at random into a virulent strain by conjugating this strain with a bacterium carrying a transposon in a manner known per se (Ely, B., *Mol. Gen. Genet.* 200, 1985, pp. 302-304). Avirulent strains resulting from the conjugation experiment may be isolated by screening for unique transposants and testing these for avirulence, for instance in the $LD_{50}$ test described in Example 1 below.

When producing avirulent strains by transposon insertion, there is slight risk that such strains may revert to wild-type, that is, excise the transposon DNA and once more become virulent. It should be noted, however, that strains according to the present invention produced by transporon mutagenesis have been tested for reversion by growth for 500 generations and no such reversion has occurred. Strains which cannot revert to wild-type may be produced by partially or completely deleting a gene which produces a product essential for bacterial virulence or a promoter or regulatory system for this gene. In order to make such a deletion, it may be necessary first to identify the gene of interest. This may, for instance, be done by identifying the site of the transposon in a successfully transposed mutant by hybridization according to conventional methods (Maniatis et al., in *Molecular Cloning. A Laboratory Manual*, Cold Spring Harbor, 1982) including isolating a DNA fragment carrying part of the transposon and part of the gene by means of a synthetic homologous oligomeric sequence, and using this fragment as a probe to screen for the wild-type by conventional hybridization methods (cf. Southern, *Methods in Enzymology* 68, 1980, pp. 151-176). Once the relevant gene has been identified, it is possible to delete it partially or completely, for instance by using appropriate restriction enzymes, site-directed mutagenesis by homologous recombination with a synthetic oligonucleotide containing fewer base pairs than the DNA fragment on the gene with which it is homologous (e.g. as described by Chan and Smith, *Nucl. Acids Res.* 12, 1984, pp. 2407-2419, or G. Winter at al., *Biochem. Soc. Trans.* 12, 1984, pp. 224-225) or by introducing directly repeated nucleotide sequences at either end of the gene and selecting for mutants in which the gene has been removed by recombinational excision. Once such defective genes have been prepared, they may be inserted into the site of intact genes in virulent strains by homologous recombination in order to produce further avirulent strains.

It is contemplated that avirulent, invasive mutant strains may be produced in this way from any of the known fish pathogenic bacteria, examples of which are strains of *Vibrio anguillarum, Vibrio salmonicida, Vibrio ordalii, Aeromonas salmonicida* ssp. salmonicida or acromogenes, *Aeromonas hydrophila, Flexibacter columnaris*, Cytophaga spp., Flavorbacterium spp., *Renibacterium salmoninarum*, Lactobacillus spp., *Edwardsiella tarda*, Pseudomonas spp., Pasteurella spp., Sporocytophaga spp., Mycobacterium spp., *Nocardia asteroides*, Streptomyces spp., Streptococcus spp., *Eubacterium tarentellus* and *Yersinia ruckerii*. A currently preferred fish pathogen is *V. anguillarum*.

Samples of specific isolated avirulent strains of *V. anguillarum* according to the invention were deposited in accordance with the provisions of the Budapest Treaty for the International Recognition of the Deposit of Microorganisms for the Purposes of Patent Procedure on Mar. 31, 1988, in Deutsche Sammlung von Mikroorganismen (DSM), Mascheroder Weg 1B, Braunschweig, Federal Republic of Germany with the following accession numbers:

TABLE III

| Time in minutes | Proportions A 2 g/l | Proportions Ex 2 2 g/l |
|---|---|---|
| R | 0.51 | 0.85 |
| 0 | 0 | 0 |
| 1 | 0 | 72 |
| 5 | 10 | 87 |
| 15 | 19 | 89 |
| 30 | 30 | 90 |
| 60 | 45 | 95 |

It will, however, be evident to persons skilled in the art that other avirulent mutants of this or another fish pathogenic bacterium may be isolated in a similar fashion, using the selection criteria and procedures indicated above and described in the examples without departing from the spirit and scope of the present invention.

It is further contemplated that the mutant strain of the invention may be one which carries a DNA sequence coding for an antigenic determinant from another fish pathogen such as a bacterium or a virus and is capable of expressing said DNA sequence. Said DNA sequence may have any suitable length, including a sequence encoding a single epitope up to a sequence coding for the entire antigen. The antigenic determinant expressed from the sequence need not be a virulence determinant, but may be any determinant which gives rise to a relevant immune response in the fish to which the vaccine is administered. Thus, the determinant may for instance be selected from bacterial endo- or exotoxins, adhesins or viral envelope proteins or fragments thereof.

Pathogens from which the antigenic determinant may be derived may be selected from A. Bacterial pathogens of fish and the diseases associated with them.

TABLE IV

Percentages of the elimination of $H_2S$ as a function of time.

| Time in minutes | Products Ex. 6 | C | Ex. 7 | D |
|---|---|---|---|---|
| 0 | 0 | 0 | 0 | 0 |
| 5 | 25 | 5 | 6 | 5 |
| 15 | 39 | 14 | 18 | 17 |
| 30 | 71 | 24 | 24 | 21 |
| 60 | 87 | 33 | 38 | 32 |

B. Viruses of fish

| Virus | Group |
|---|---|
| Infectious Pancreatic Necrosis Virus | Reovirus-like |
| Infectious Hematopoietic Necrosis Virus | Rhabdovirus |
| *Herpesvirus salmonis* | Herpesvirus |
| Channel Catfish Virus | Herpesvirus |
| NeVTA Virus | Herpesvirus |
| *Onchorhynchus masou* Virus | Herpesvirus |
| Lymphocytis Virus | Iridovirus |
| Carp Gill Necrosis Virus | Iridovirus-like |
| Bluegill Virus | Orthomyxovirus |

| Virus | Group |
| --- | --- |
| Eel Virus 2 | Orthomyxovirus |
| Eel Virus A | Rhabdovirus |
| Eel Virus X | Rhabdovirus |
| Viral Hemorrhagic Septicemia Virus | Rhabdovirus |
| Spring Viremia of Carp Virus | Rhabdovirus |
| Pike Fry Rhabdovirus | Rhabdovirus |
| Golden Shiner Virus | Reovirus-like |
| Eel Virus E | Reovirus-like |
| Chum Salmon Virus | Reovirus |
| Eel Virus 1 | Ungrouped |
| Grunt Fin Agent | Ungrouped |

(Both tables are shown in Jorge H. Crosa (ed.), Bacterial and Viral Diseases of Fish: Molecular Studies. University of Washington, Seattle, 1983).

A mutant strain carrying an antigenic determinant from another fish pathogen may be prepared according to techniques which are well established in the field of human medicine where several examples of live oral vaccines comprising an antigenic determinant expressed by another organism have been developed, e.g. a hybrid Salmonella/Shigella vaccine (Formal et al., *Infect. Immun.* 34, 1981, pp. 746–750). Two different routes may be suggested for producing a live vaccine of this type: either a gene from the fish pathogen may be isolated, characterized and tested for antigenic properties followed by insertion into a host bacterium, or genomic DNA from the fish pathogen may be shotgun-cloned into a host bacterium and one or more strains with a suitable antigenicity may subsequently be selected. In the latter case, the strains may be constructed by using as the cloning vector a broad host range plasmid capable of replicating in, for instance, *E. coli* and the desired host strain, e.g. *V. anguillarum*. The cloning vector should furthermore carry a cloning casette (i.e. a DNA sequence which comprises several restriction sites and is able to mobilize from *E. coli* to *V. anguillarum*). When constructing a gene library of the pathogen in question, genomic DNA of the pathogen is first cloned into *E. coli*, and the vector carrying this genomic DNA is subsequently transferred to, for instance, *V. anguillarum*. The hybrid bacteria may then be used to infect fish according to the procedure described above, and 2–4 weeks later, the infected fish are tested for immunity to the pathogen in question.

Although, in theory, the gene or subsequence thereof coding for the antigenic determinant may be inserted in and expressed by a bacterium which is not pathogenic to fish, it is preferred to insert it into a mutant strain of the invention in order to ensure a high degree of infectivity and to obtain immunity against two or more pathogens by means of the same vaccine. It is considered to be particularly advantageous to construct an avirulent, invasive mutant strain of the invention by inserting the gene or subsequence thereof coding for the antigenic determinant into a gene of a host pathogenic bacterium the product of which is required for bacterial pathogenicity, thus obtaining in one operation an avirulent mutant strain which confers immunity not only to the host bacterium, but also to the other fish pathogen. In a particular embodiment of the vaccine, not only one, but two or more DNA sequences coding for antigenic determinants from different fish pathogens have been inserted so as to obtain a vaccine which offers broad-spectrum protection against a range of fish pathogens.

Once a suitable mutant strain has been isolated, it may be propagated by growing the selected strain in a suitable culture medium aerobically under conditions suited for the propagation of each bacterial species for a period of time sufficient to provide at least $10^8$ bacteria per ml of medium and harvesting the resulting bacteria from the medium. The medium is suitably a rich medium such as Trypticase Soy Broth, Luria Broth, Nutrient Broth, Brain Heart Infusion Broth, or the like containing the required carbon and nitrogen sources and mineral nutrients. For cultivating seawater pathogens, the medium should additionally be supplemented with NaCl in an amount corresponding to, or slightly above, that present in seawater, typically about 1.5–2%. The cultivation temperature will typically be in the range of 18°–25° C., and the pH in the range of 6.8–7.8.

Although it is theoretically possible to add the bacteria as grown, i.e. the culture medium containing the bacteria, to the suspension in which fish are to be immersed, it is generally preferred to produce a concentrate in order to obtain a higher count of bacteria for administration. The concentrate may, for instance, be prepared by centrifugation or filtration, and the bacteria may furthermore be washed before addition to the bath. The bacterial concentrate may then be added in the wet state or may, in order to facilitate transport and long-term storage, be freeze-dried or spray-dried in a manner known per se. The resulting powder may then be added directly to the immersion bath or may be admixed with fish feed and dosed orally to the fish.

As indicated above, it has been found advantageous to immunize the fish by adding the bacterial preparation (whether wet or dried) to a suspension to which the fish are transferred for immunization purposes, since immunization by injection, although efficient in experiments, is not a commercially viable method. Thus, administration of the mutant bacteria is preferably carried out by immersing a fish in a suitable suspension of the avirulent mutant bacteria for a period of time sufficient to effect an adequate immunization. It has been found that, generally, a longer immunization time confers an improved immunity. According to the present invention, to employ immunization times of 15 minutes or more, 30 minutes having been found to confer a satisfactory immunity in the experiment described in Example 1. The suspension of avirulent, invasive mutant bacteria contains $1 \times 10^2$–$1 \times 10^8$ bacteria/ml, preferably $1 \times 10^6$–$1 \times 10^8$ bacteria/ml, a number of $1 \times 10^7$/ml–$2 \times 10^7$/ml having been found to confer an adequate immunity upon immersion of the fish for 30 minutes.

During the research leading to the present invention, the present inventors have found that fish are most likely to be exposed to infections caused by virulent pathogens when the temperature of the water increases to 18° C. or more (this at least being the case for *V. anguillarum*). This pattern of infectivity makes it advantageous to administer the vaccine of the invention at least once a year at a time of year when the risk of infection by fish pathogens is particularly high, or preferably immediately before this period. The dosage administered may then confer an adequate protective immunity against the infection in question for the entire period where the risk of infection is high (typically the summer months) or, if not, it may be followed up at some suitable point with one or more booster immunizations. The immunization of fish by immersion is advantageously carried out by using a suspension of the avirulent, invasive mutant strain which has a temperature of 0°–25° C., preferably 0°–18° C., in which suspension the NaCl concentration is at least 0.3% (w/w). The efficiency of the immunization may conveniently be tested by the $LD_{50}$ test described above.

In accordance with the invention, it may be particularly advantageous to immunize fish fry, i.e. fish with a weight of from about 3–5 g to about 20 g with the vaccine of the invention as these seem more susceptible to fish pathogens than adult fish.

Although, as indicated above, it is preferred for various reasons to use a live vaccine of the invention to immunize fish, it is contemplated that it is possible to use the avirulent mutant strain of the invention in a killed vaccine. Hence, the invention further relates to a killed vaccine for the immunization of fish against diseases caused by fish pathogens, which comprises a killed avirulent immunogenic mutant strain of a fish pathogenic bacterium. The bacteria used in the vaccine may be killed by any of the methods generally employed in the vaccine field, such as by treatment with formalin. The bacteria may otherwise exhibit the traits described above for the mutant

EXAMPLE 1

Preparation of an avirulent, invasive mutant of *V. anguillarum* and its use as a live vaccine

Materials and Methods

Bacterial strains: The strains used in this study and their sources are listed in Table 1.

TABLE 1

| Strain | Source | Markers |
|---|---|---|
| V. anguillarum 775 | U.B.S. Sørensen and J.L. Larsen, "Serotyping of *Vibrio anguillarum*." Appl. Environ. Microbiol. 51, 1986, pp. 593–597. | |
| 775.17B | This study | $Rif^r$, $Str^r$-derivative of 775* |
| 6018/1 | Sørensen and Larsen, supra | |
| 53-507 | Sørensen and Larsen, supra | |
| ATCC 19264 | Publicly available from the ATCC | |
| NB 10** | This study | |
| NB 15 | This study | $Rif^r$, $Ste^{r*}$ |
| E. coli K 12/C 600 | Ely, B. 1985. Vectors for transposon mutagenesis of non-enteric bacteria. Mol. Gen. Genet. 200, pp. 302–304 | pRK2013: Tn5/132 $Tet^r$, $Amp^{r***}$ |

*chromosomal resistance to rifampicin and streptomycin; obtained as a spontaneous mutant by selection on TSA plates containing rifampicin (200 μg/ml) and streptomycin (100 μg/ml).
**isolated from the kidney of a rainbow trout dead from an epizootic vibrosis at a fish farm in the northern Gulf of Bothnia.
***plasmid resistance to tetracycline and ampicillin.

Isolation and characterization of strain 775: The strain was isolated from a diseased fish (*Onchorhynchus kisutsch*). Swabs were inoculated on blood agar plates that were incubated for 48 hours at 25° C. Typical bacterial colonies resembling *V. anguillarum*, i.e. low convex, semitranslucent, and hemolytic, were isolated for primary identification according to the following characteristics: gram-negative motile rods which were sensitive to the vibriostatic agent 0/129 (2,4-diamino-6,7-diisopropylpteridine, 10 μg/disc); catalase- and oxidase-positive; positive in the nitrate reduction and arginine decarboxylate tests; negative for lysine and ornithine decarboxylases; fermentative in the oxidation-fermentation test and able to grow in 6% NaCl but not in 7% NaCl. The strain belongs to the serotype 01 according to the system described by Sorensen and Larsen, supra.

Conjugation and transposition experiments: Plasmid pRK2013 was transferred from *E. coli* K 12 C600/pRK2013:Tn5-132 by conjugation on filters (Walter et al. 1975). The donor (*E. coli*) and the recipient (*V. anguillarum*) were grown overnight in Luria Broth (*E. coli*) or Brain Heart Infusion Broth supplemented with 2% NaCl (*V. anguillarum*). The strains were inoculated in fresh media and grown to $1 \times 10^8$ bacteria per ml. A mixture containing 1.5 ml donor and recipient respectively was passed through a 0.45 m membrane filter. The filter was placed on Trypticase Soy Agar (TSA) plates supplemented with 2% NaCl for 3 hours at 18° C. After incubation, the filters were transferred to TSA plates supplemented with 2% NaCl containing tetracycline (15 μg/ml) rifampicin (200 μg/ml) and streptomycin (100 μg/ml) to select for *V. anguillarum* exconjugants. Colonies appearing on the plates was transferred to new TSA plates plus 2% NaCl plus tetracycline, rifampicin and streptomycin. After incubation, the exconjugants were frozen at −70° C. before use in experimental fish infections. Protease determination: Detection of protease activity was performed by patching the bacteria on Frazier-gelatin plates (Rodina, 1972) supplemented with 2% NaCl. After incubation at 18° C. for 24 hours, the plates were flooded with 12.5% $HgCl_2$ in 1M HCl. A transparent zone around the colony indicated proteolytic activity.

Hemolysin determination: Presence of hemolytic activity was determined by patching the bacteria on Nutrient Broth (Oxoid) supplemented with 5% horse blood and 2% NaCl.

Blotting and hybridization procedures: Chromosomal DNA, digested with EcoR1 and fractionated on agarose gels, was transferred to nitrocellulose filters, hybridized with a $^{32}P$-labeled probe prepared by 5' end-labelling, and washed (Maniatis et al., 1982). The probe used was a 30-mer synthetic oligonucleotide, complementary to part of the $IS_L$ of Tn5 (Symbicom, Ume å, Sweden).

Iron requirements: Exconjugants were tested for the ability to sequester iron by patching them on M9 plates supplemented with 2% NaCl and 25M EDDA (ethylenediamine-di(o-hydroxyphenyl) acetic acid).

Experimental fish infections: Virulence tests were carried out on rainbow trout (*Salmo gairdneri*) with a weight of 5–15 grams. The bacteria was administered either by intraperitoneal injection (i.p.) or by immersion (im.). For each bacterial dilution tested, five fishes were used. The bacteria were 24-hours cultures grown in Trypticase Soy Broth (TSB) supplemented with 2% NaCl at 18° C. In the i.p. experiments, the fishes were anaesthetized with tricaine methane sulphonate (100 mg/liter) and inoculated subcutaneously in the peritoneal cavity. The immersion infections were performed by adding bacteria to the aquarium in which the fishes were swimming. After 30 minutes, fresh brackish water was added, after which the fishes were maintained in brackish water for 7 days. Dead fishes were collected each day and kidney samples were tested for the presence of bacteria. Virulence was expressed as the 50% lethal dose ($LD_{50}$) (Reed and Muench, 1938). Immunization experiments: Fish were immersed in $2 \times 10^7$ bacteria/ml of *V. anguillarum* exconjugants, VAN 20 or VAN 70, for 30 minutes at 18° C. The fish were transferred to tanks in which they were held. Challenges were performed 1, 2, 4, 10 and 17 weeks after the initial immunization. The bacterial strains used for challenge were 775.17B and NB 10. The challenge was performed as described in the preceding sections by immersion with three successive 10-fold dilutions of the bacteria. Booster immunizations were carried out after 12 weeks in the same way as the initial immunizations.

RESULTS

LD$_{50}$ measurements of different isolates of *Vibrio anguillarum*

The 50% lethal dose of different isolates of *Vibrio anguillarum* was tested both by injecting the bacteria intraperitoneally (i.p.) or by immersing (im.) the fish in water containing bacteria. One strain of *Escherichia coli* was used as a negative control.

TABLE 2

Determination of LD$_{50}$ values of different isolates of *Vibrio anguillarum*.

| Isolate | LD$_{50}$ i.p. | LD$_{50}$ im. |
|---|---|---|
| 775 | $<1 \times 10^2$ | $2 \times 10^5$ |
| 53-507 | $4 \times 10^3$ | $2 \times 10^7$ |
| ATCC 19264 | $1 \times 10^4$ | $<5 \times 10^7$ |
| 6018/1 | $2 \times 10^3$ | $>5 \times 10^7$ |
| NB 15 | $<1 \times 10^2$ | $5 \times 10^7$ |
| *E. coli* C600 | $4 \times 10^6$ | ND*/ |

*/not determined

One isolate (775) was significantly more virulent after immersion than the other tested isolates. Therefore, strain 775 was chosen for further studies, since one aim with the present investigation was to create live vaccine strains which could be distributed by immersion.

Construction of mutants

*Vibrio anguillarum* 775.17B was mated with *E. coli* C600/pRK2013:Tn5-132 harbouring the transposon Tn5-132 (tetracycline resistance). Tn5-132 is carried on a transposon delivery vector derived from pRK2013. Since pRK2013 is based on the ColEi replicon and has a broad host range transfer system, it can be transferred to, but is unable to replicate in, many non-enteric gram-negative bacteria (Ely, 1985). Conjugations were performed on filters which gave a frequency of transposition of about $10^{-7}$. The donor and recipient were mixed on a filter and placed on non-selective media for 3 hours. The filter was transferred to a selective plate and incubated at 18° C. Since the filters were incubated on the selective media, each colony that appeared was certain to be a unique exconjugant. The exconjugants were picked and streaked on a new selective plate. In parallel the recipient strain, 775.17B, was also passaged the same number of times on plates, to ensure that an eventual change in pathogenicity within the exconjugants was not a result of too many passages. Plasmid preparation of the exconjugants showed that the delivery plasmid vector pRK2013 did not replicate in strain 775.17B (data not shown).

Screening for avirulent exconjugants

Exconjugants were screened for virulence by infecting rainbow trout as described above. The challenge was carried out by immersing fish in water containing $5 \times 10^6$ bacteria per ml for 30 minutes. Mortality was monitored daily and the experiments were run for 7 days.

Two of the tested mutants were found to be avirulent. These two mutants, VAN 20 and VAN 70, were further tested for their virulence by infecting fish both intraperitoneally and by immersion.

LD$_{50}$ (i.p.) exceeded $1 \times 10^6$ bacteria and LD$_{50}$ (im.) exceeded $2 \times 10^7$ bacteria per ml for both strains. The corresponding LD$_{50}$ values for the parent strain were $<1 \times 10^2$ and $2 \times 10^5$ (Table 2).

Characterization of exconjugants

Production of proteases and hemolytic activity has been suggested to be involved in the pathogenicity of bacteria. V. anguillarum exhibits both a proteolytic and a hemolytic activity. The ability of all isolated exconjugants to produce proteolytic activity was tested by patching the bacteria on a gelatin plate. None of the isolated exconjugants lacked protease activity.

Examination of the hemolytic activity on blood plates also gave positive results in all cases.

The ability to sequester low amounts of iron from the host has also been a factor suggested to be involved in virulence. The exconjugants were therefore tested on minimal plates containing the iron chelator EDDA. All exconjugants were able to grow on the plates, indicating that the transposon had not been incorporated in the 65 kb plasmid known to encode for an iron sequestering system. The plasmid was isolated from the exconjugants, whereafter the plasmid was digested with BamH1. No difference was observed when the digestion pattern of the plasmid of strain 775.17B was compared to the corresponding plasmid of the exconjugants. Thus, in no case the transposon had been incorporated into the 65 kb plasmid.

The growth rate of the bacteria is a factor which might effect the virulence. To study whether the incorporation of the transposon changed the growth rate of the exconjugants, the two avirulent plus four virulent exconjugants and the wild type strain were grown in MOPS minimal media (Neidhardt et al., 1974) at 20° C. The wild type strain, 775.17B, grew faster than the mutants, but no correlation could be observed between growth rate and degree of virulence among the exconjugants (Table 3).

TABLE 3

The growth rate of exconjugants and the wild type strain in MOPS minimal media

| | VAN 1 | VAN 2 | VAN 6 | VAN 7 | VAN 20 | VAN 70 | 775 17B |
|---|---|---|---|---|---|---|---|
| Growth rate (min.) | 226 | 189 | 254 | 243 | 219 | 240 | 186 |

Figure 1:
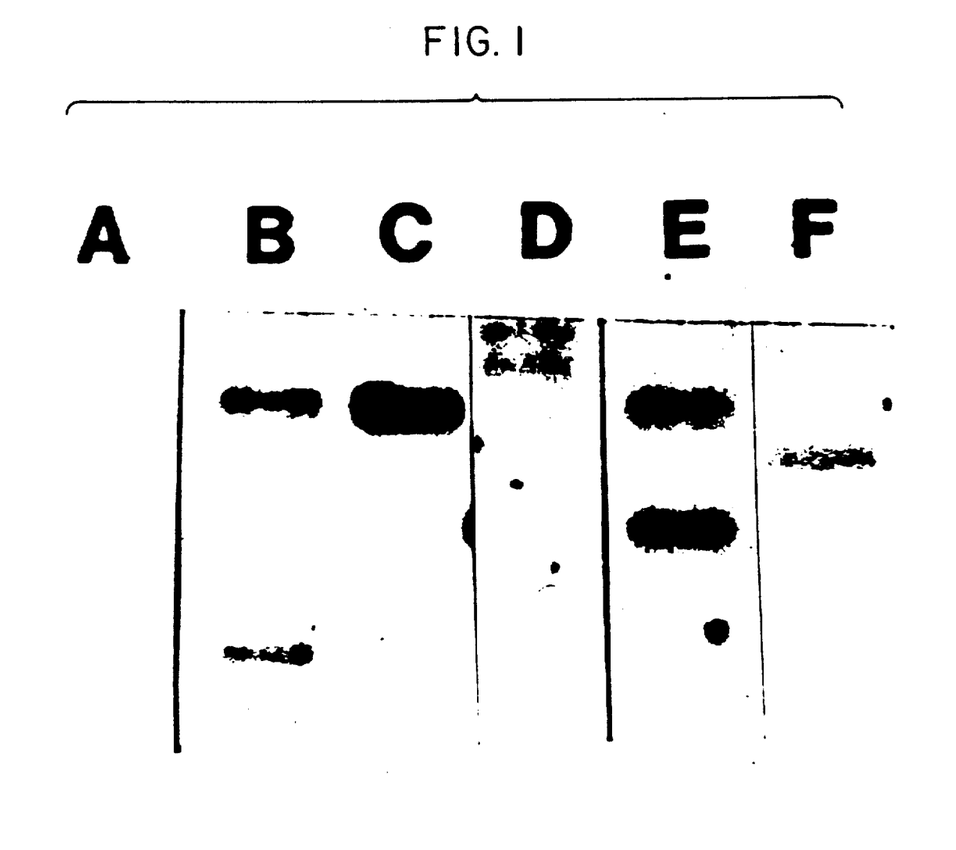
FIG. 1: Southern blot hybridization demonstrating random integration of transposon Tn5-132 into the strain 775 chromosome. Lane designations: unlabeled (left side)—strain 775; A—VAN 1; B—VAN 2; C—VAN 6; D—VAN 7; E—VAN 20; F—VAN 70.

In order to investigate if the transposon had been incorporated randomly into the chromosome, chromosomal DNA of six different exconjugants were isolated digested with EcoR1, and separated on an agarose gel. The DNA was then transferred to a nitrocellulose filter. Filter hybridization was performed by the use of a $^{32}$P-labeled oligonucleotide, which had complete homology to nucleotides 49 to 78 in the inverted repeat of Tn5-132. All six exconjugants showed different hybridization patterns (FIG. 1). Tn5-132 has an EcoR1 site in the middle of the transposon, explaining the appearance of two bands in each lane. The parent strain 775 was also digested and blotted but no hybridization was observed. Thus, it can be concluded that the transposon had been incorporated randomly into the chromosome of the different exconjugants.

Use of avirulent exconjugants as vaccines

The two avirulent exconjugants, VAN 20 and VAN 70, were tested for their potential ability as live vaccines against vibriosis. Fish were immersed in a bacterial suspension, containing either VAN 20 or VAN 70, at a concentration of $2 \times 10^7$ bacteria per ml for 30 minutes at 18° C. Challenge was performed 1, 2, 4, 10 and 17 weeks after vaccination. Two different strains were used as challenge organisms, the homologous 775.17B and a heterologous strain NB 10. The latter strain exhibits a very low $LD_{50}$ value when the fish are infected by immersion. The challenge was carried out by bathing the fish in water containing three different concentrations of the test strains. This made it possible to determine the $LD_{50}$ values of the vaccinated fish compared to non-vaccinated fish. Two weeks after immunization, the vaccinated fish showed an increased resistance against the homologous strain, observed as a 10 to 30-fold increase in the $LD_{50}$ value (Table 4).

TABLE 4

Numbers per ml of strain 775.17 and strain NB 10 causing 50% mortality of vaccinated or non-vaccinated rainbow trout (*Salmo gairdneri*) 1, 2, 4, 10 and 17 weeks after immunization

| weeks after immun. | vacc. strain $LD_{50}$ (bact./ml) | | |
|---|---|---|---|
| | none | VAN 20 | VAN 70 |
| */ | | | |
| 1 | $3 \times 10^6$ | $5 \times 10^6$ | $3 \times 10^6$ |
| 2 | $2 \times 10^6$ | $2 \times 10^7$ | $6 \times 10^7$ |
| 4 | $5 \times 10^6$ | $5 \times 10^7$ | $9 \times 10^6$ |
| 10 | $5 \times 10^6$ | $5 \times 10^7$ | $3 \times 10^7$ |
| 12 | | BOOSTER | BOOSTER |
| 17 | $2 \times 10^6$ | $3 \times 10^6$ $9 \times 10^7$ | $2 \times 10^6$ $1 \times 10^8$ |
| #/1 | | | |
| 17 | 5 | 10    10 | 8    $2 \times 10^5$ |

\* = challenge with 775.17
# = challenge with NB 10

After 4 weeks, the protection was still significant and even after 10 weeks, the protection was held on the same level. When the immunized fish were challenged with the heterologous strain NB 10, a weak positive effect was also observed. 12 weeks after the immunization, a booster dose was administered. After 17 weeks, the non-boostered fish were no longer protected. However, the boostered fish showed high levels of protection. It should be noted that protection against NB 10 (i.e. the heterologous strain) was observed in the VAN70 boostered fish.

Based on these results, the following conclusions can be drawn:

1) It was possible to produce avirulent mutants by transposing the transposon Tn5-132 into *Vibrio anguillarum* by using the broad host range delivery vector pRK2013. The vector could not replicate in *V. anguillarum*.
2) The transposon was incorporated randomly into the chromosome of the recipient.
3) It was possible to isolate exconjugants which were avirulent to rainbow trout in laboratory infection experiments.
4) The avirulent mutants were not affected in any of the tested potential virulence properties.
5) The use of the avirulent exconjugants as live vaccines gave an increased resistance both to homologous and heterologous pathogenic agents.

EXAMPLE 2

The strain VAN1000 was isolated as a streptomycin and rifampicin resistant spontaneous mutant of *V. anguillarum* 775.17B by selection on TSA plates supplemented with 200 μg/ml of rifampicin, followed by selection on TSA plates supplemented with 100 μg/ml of streptomycin substantially as described in Example 1.

The isolated strain was subjected to $LD_{50}$ measurements as described in Example 1. The $LD_{50}$ was greater than $1 \times 10^8$/ml.

Immunization experiments were carried out as described in Example 1 by immersing fish in water containing $1 \times 10^7$/ml of VAN1000. The results, which were measured by determining the increase in the $LD_{50}$ value, are shown in Table 5.

TABLE 5

| Weeks after immunization | | Strain *V. anguillarum* 775.17B $LD_{50}$ (per ml) | | Strain *V. anguillarum* NB 10 $LD_{50}$ (per ml) | | Strain *A. salmonicida*\* $LD_{50}$ (per ml) | |
|---|---|---|---|---|---|---|---|
| | | control | vacc. | control | vacc. | control | vacc. |
| Exp 1 | 1 | $2 \times 10^6$ | $1 \times 10^8$ | <10 | $7 \times 10^5$ | $1 \times 10^2$ | $2 \times 10^5$ |
| | 2 | $5 \times 10^5$ | $1 \times 10^8$ | <10 | $1 \times 10^6$ | | |
| | 3 | $2 \times 10^5$ | $>7 \times 10^8$ | <10 | $8 \times 10^6$ | $1 \times 10^2$ | $2 \times 10^5$ |
| Exp 2 | 4 | $5 \times 10^6$ | $>5 \times 10^8$ | | | | |
| | 10 | $3 \times 10^6$ | $>3 \times 10^8$ | <10 | $3 \times 10^5$ | | |
| | 12 | | | | | $1 \times 10^2$ | $2 \times 10^5$ |
| | 17 | $4 \times 10^6$ | $>4 \times 10^8$ | <10 | $>3 \times 10^7$ | | |

\*A wild-type strain obtained isolated from an outbreak of furunculosis in the Baltic.

It appears from Table 5 that VAN1000 not only confers protection against a homologous and heterologous strain of *V. anguillarum*, but also cross-protection against *A. salmonicida*.

EXAMPLE 3

A field immunization trial was carried out using the strain VAN1000. In January 1988, 200 rainbow trout (*Salmo gairdneri*) were vaccinated as described in Examples 1 and 2 by immersing the fish in water containing $1 \times 10^7$/ml of the above strain for 30 minutes at a temperature of 18° C. The vaccinated fish were kept in 1 m³ trays from the time of vaccination until September 1988. Unvaccinated fish which were kept in two other trays (2000 and 1000 fish, respectively) served as controls.

The incoming water was unpurified brackish water from the Baltic Sea, and the water was the only source of infection. The water inlet was shared by all three trays.

Outbreaks of vibriosis were monitored in the trays by recording the number of fish dying in each individual tray. The disease was confirmed by isolating *Vibrio anguillarum* from a representative number of dead fish. Outbreaks of fatal vibriosis occurred during July at two different occasions in the two trays with unvaccinated fish. No significant deaths of fish were observed after the month of July in the control groups. In the vaccinated group of fish, however, only 1 fish died in the beginning of the month, during which period outbreaks were not observed in the control trays. During the outbreaks in the unvaccinated fish groups, no deaths occurred in the vaccinated fish.

Figure 2:
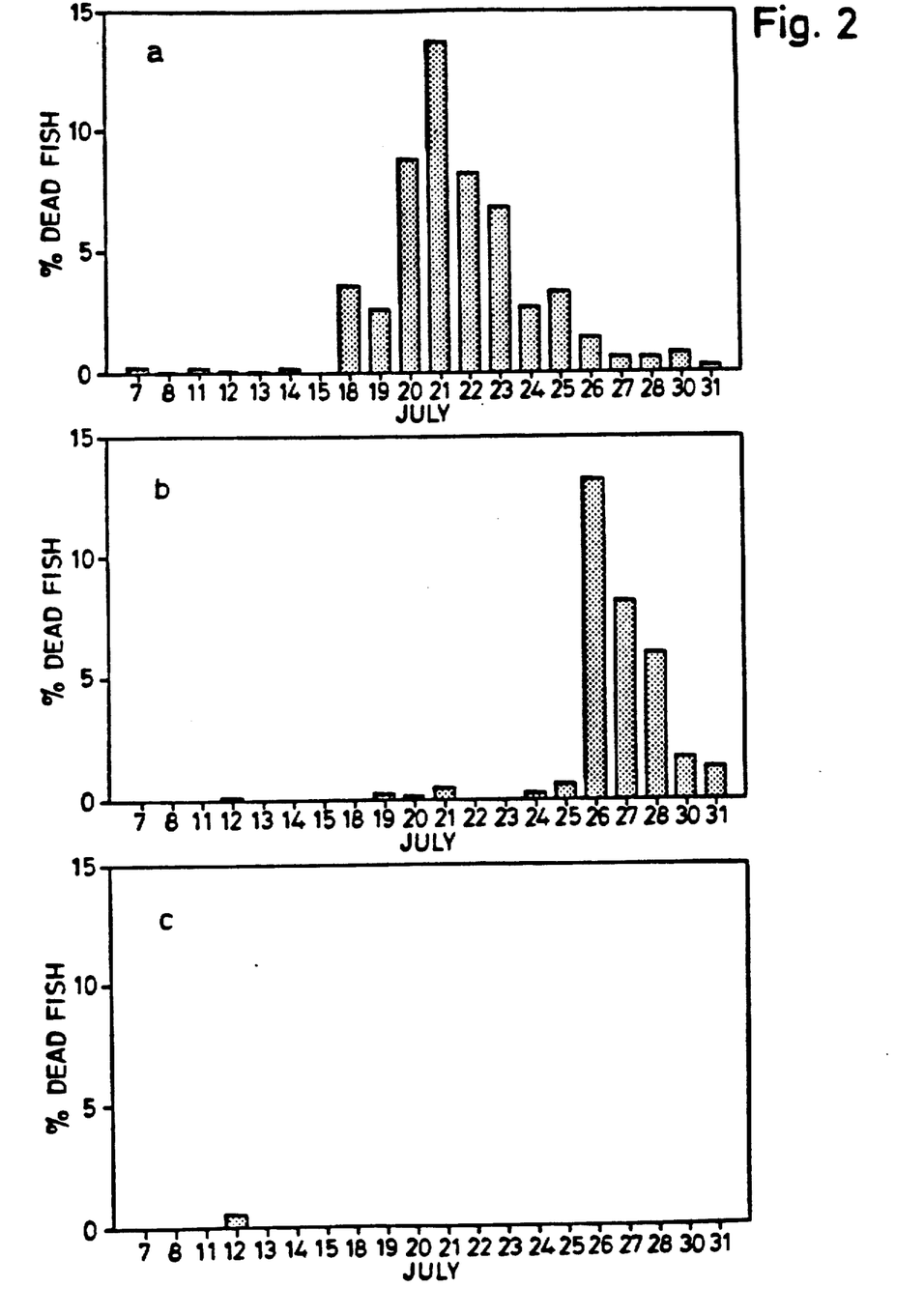
FIG. 2: Vibriosis fatalities of rainbow trout treated with unpurified brackish water from the Baltic sea. Panel a: 200 unvaccinated fish; Panel b: 1000 unvaccinated fish; Panel c: 200 VAN 1000-vaccinated fish.

The results are illustrated in FIG. 2, in which the number of dead fish are given as a percentage of the total number of live fish in the trays. In the figure, a denotes unvaccinated fish in tray No. 1; b denotes unvaccinated fish in tray No. 2; and c denotes vaccinated fish.

In conclusion, the VAN1000 strain has conferred a significant protection against a natural infection challenge under field conditions in susceptible rainbow trout.

LITERATURE

Agius, C., M. T. Horne, and P. D. Ward, 1983. Immunisation of rainbow trout, *Salmo gairdneri* Richardson, against vibriosis: comparison of an extract antigen with whole cell bacterins by oral and intraperitoneal routes. *J. Fish Dis.* 6: pp. 129–134.

Crosa, J. H. 1980. A plasmid associated with virulence in the marine fish pathogen *Vibrio anguillerum* specifies an iron-sequestering system. *Nature* 284, pp. 566–568.

Ely, B. 1985. Vectors for transposon mutagenesis of non-enteric bacteria. *Mol. Gen. Genet.* 200, pp. 302–304.

Hone, D., R. Morona, S. Attridge, and J. Hackett, 1987. Construction of defined galE mutant of *Salmonella* for use as vaccines. *J. Inf. Dis.* 156, pp. 167–174.

Inamura, H., K. Muroga, and T. Nakai, 1984. Toxicity of extracellular products of *Vibrio anguillarym, Fish Pathol.* 19, pp. 89–96.

Inamura, H., T. Nakai, and K. Muroga, 1985. An extracellular protease produced by *Vibrio anguillarum. Bull. Jap. Soc. Sci. Fish.* 51, pp. 1915–1920.

Kawano, K., T. Aoki, and T. Kitao, 1984. Duration of protection against bvibriosis. in ayu, Plecoglossus altivelis, vaccinated by immersion and oral administration with *Vibrio anguillarum. Bull. Jpn. Soc. Sci. Fish.* 50, pp. 771–774.

Kodama, H., M. Moustafa, S. Ishiguro, T. Mikami, and H. Izawa, 1984. Extracellular virulence factors of fish Vibrio: Relationships between toxic material, haemolysin and proteolytic enzyme. *Am. J. Vet. Res.* 45, pp. 2203–2207.

Maniatis, T., E. F. Fritsch, and J. Sambrook, 1982. Molecular cloning. A laboratory manual. Cold Spring Harbor, N.Y.

Munn, C. B., 1978. Haemolysin production by *Vibrio anguillarum. FEMS Microbiol. Lett.* 3, pp. 265–268.

Neidhardt, P. C., P. L. Bloch, and D. F. Smith, 1974. Culture medium for enterobacteria. *J. Bacteriol.* 119, pp. 736–747.

Reed, L. J., and H. Muench, 1938. A simple method on estimating fifty per cent endpoints. *Am. J. Hyg.* 27, pp. 493–497.

Rodina, A. G., 1972. Methods in aquatic microbiology, pp. 254–255.

Trust, T. J., I. D. Courtice, A. G. Khouri, J. H. Crosa, and M. H. Schiewe, 1981. Serum resistance and haemagglutination ability of marine vibrios pathogenic to fish. *Infect. Immun.* 34, pp. 702–707.

Wahden, M. H., C- Se'rie', Y. Cerisier, S. Sallam, and R. Germanier, 1982. A controlled field trial of live *Salmonella typhy* strain Ty 21a oral vaccine against typhoid: three-year results. *J. Inf. Dis.* 145, pp. 292–295.

Walter, M. A., S. A. Potter, and J. H. Cross, 1983. Iron uptake system mediated by *Vibrio anguillarum* plasmid pJM1. *J. Bacteriol.* 156, pp. 880–887.

Ward, P. D., M. F. Tatner, and M. T. Horne, 1985. Factors influencing the efficacy of vaccines against vibriosis caused by *Vibrio anguillarum*. In "Fish Immunology". M. J. Manning and M. F. Tatner (eds.), pp. 221–229.

Wolf, M. K., and J. H. Crosa, 1986. Evidence for the role of a siderophore in promoting *Vibrio anguillarum* infections. *J. Gen. Microbiol.* 132, pp. 2949–2952.

We claim:

1. A live fish vaccine comprising an avirulent, invasive and immunogenic mutant strain of a fish bacterium selected from the group consisting of a Vibrio species or an Aeromonas species in isolated form, wherein said fish bacterium carries at least one antibiotic-selectable marker and said fish bacterium grows in the presence of an iron chelator, said fish vaccine conferring on fish immunized therewith protection against diseases caused by homologous and heterologous Vibrio and Aeromonas fish pathogens.

2. A live fish vaccine according to claim 1, wherein said fish bacterium is a strain of Vibrio spp.

3. A live fish vaccine according to claim 1, wherein said fish bacterium is a strain of Aeromonas spp.

4. A live fish vaccine according to claim 2, wherein said fish bacterium is one which grows in the presence of an iron chelator.

5. A live fish vaccine according to claim 4, wherein said fish bacterium is selected from the group of strains consisting of VAN 1000, VAN 70, and VAN 20.

6. A live fish vaccine according to claim 1, wherein said fish bacterium carries markers selectable against at least two different antibiotics.

7. A live fish vaccine according to claim 1, which confers immunization protection when said fish are immersed in an aqueous solution containing said fish bacterium.

8. A live fish vaccine according to claim 1, wherein a parental strain of said fish bacterium was treated with a mutagen.

9. A live fish vaccine according to claim 1, wherein a gene in said fish bacterium, the expression product of which is required for bacterial virulence, is defective or absent.

10. A live fish vaccine according to claim 9, wherein said gene codes for a virulence determinant.

11. A live fish vaccine according to claim 9, wherein said gene contains a heterologous DNA insertion.

12. A live fish vaccine according to claim 9, wherein said gene is partially deleted.

13. A live fish vaccine according to claim 10, wherein the gene contains a heterologous DNA insertion.

14. A live fish vaccine according to claim 10, wherein said gene is partially or completely deleted.

15. A live fish vaccine according to claim 11, wherein said heterologous DNA insertion is a transposon insertion.

16. A live fish vaccine according to claim 15, wherein said gene containing said heterologous DNA insertion is a chromosomal gene.

17. In isolated form, an avirulent, invasive and immunogenic mutant strain of a living fish bacterium selected from the group consisting of a Vibrio species or an Aeromonas species, wherein said fish bacterium carries at least one antibiotic-selectable marker and grows in the presence of an iron chelator, said fish bacterium conferring on fish immunized therewith protection against diseases caused by homologous and heterologous Vibrio and Aeromonas fish pathogens.

18. A fish bacterium according to claim 17, which is a fish bacterium of Vibrio spp.

19. A fish bacterium according to claim 17, which is a fish bacterium of Aeromonas spp.

20. A fish bacterium according to claim 18, which can grow in the presence of an iron chelator.

21. A fish bacterium according to claim 18, which is a *Vibrio anguillarum* strain selected from the group of strains consisting of VAN 1000, VAN 20 and VAN 70.

22. A fish bacterium according to claim 17, which carries markers selectable against at least two different antibiotics.

23. A fish bacterium according to claim 17, wherein a parental strain of said fish bacterium was treated with a mutagen.

24. A fish bacterium according to claim 17, in which a gene, the product of which is required for bacterial virulence, is defective or absent.

25. A fish bacterium according to claim 24, wherein said gene codes for a virulence determinant.

26. A fish bacterium according to claim 25, wherein said gene contains a DNA insertion.

27. A fish bacterium according to claim 24, wherein said gene is partially deleted.

28. A fish bacterium according to claim 24, wherein said gene contains a heterologous DNA insertion.

29. A fish bacterium according to claim 25, wherein said gene is partially or completely deleted.

30. A fish bacterium according to claim 28, wherein said heterologous DNA insertion is a transposon insertion.

31. An fish bacterium according to claim 30, wherein said gene containing said heterologous DNA insertion is a chromosomal gene.

* * * * *

UNITED STATES PATENT AND TRADEMARK OFFICE
CERTIFICATE OF CORRECTION

PATENT NO. : 5,284,653    Page 1 of 3
DATED : February 8, 1994
INVENTOR(S) : Wolf-Watz et al.

It is certified that error appears in the above-identified patent and that said Letters Patent is hereby corrected as shown below:

On Cover page, OTHER PUBLICATIONS, Column 2, line 1, "Virbiosis" should read --Vibriosis--; and
line 20, "1985,," should read --1985,--.

Page 2, OTHER PUBLICATIONS", Column 1, line 5, "anguillarym" should read --anguillarum--;
line 8, "anguillarym" should read --anguillarum--;
line 11, "Aeronmonas" should read --Aeromonas--;
line 14, "bvibriosis" should read --vibriosis--; and
line 19, "salmonicida" should read --Salmonicida--.

Column 2, line 17, "*typhy*" should read --*typhi*--;
line 20, "Iton" should read --Ion--;
line 21, "anguillarym" should read --anguillarum--; and
line 24, "vibriosis" should read --Vibriosis--.

Column 2, line 62, "200" should read --2000--.

Column 5, line 60, "Flavorbacterium" should read --*Flavobacterium*--;

Column 6, delete in the entirety "TABLE III" (lines 8-19) and replace with the following table to begin on line 8:

-- VAN 20      DSM 4506
   VAN 70      DSM 4507
   VAN 1000    DSM 4508 --

UNITED STATES PATENT AND TRADEMARK OFFICE
CERTIFICATE OF CORRECTION

PATENT NO. : 5,284,653

DATED : February 8, 1994

INVENTOR(S) : Wolf-Watz et al.

It is certified that error appears in the above-identified patent and that said Letters Patent is hereby corrected as shown below:

Column 6, delete in the entirety "TABLE IV" (lines 46-55), and replace with the following table to begin on line 46:

| --Bacterium | Disease |
|---|---|
| Aeromonas salmonicida | Furunculosis |
| Aeromonas hydrophila | Motile aeromonas septicemia |
| Yersinia ruckeri | Enteric redmouth |
| Vibrio anguillarum | Virbriosis |
| Vibrio ordalii | Virbriosis |
| Flexibacter columnaris | Columnaris |
| Cytophaga psychrophila | Low temperature disease |
| Cytophaga or Flavobacterium | Bacterial gill disease |
| Renibacterium salmoninarum | Bacterial kidney disease |
| Lactobacillus sp. | Pseudokidney disease |
| Edwardsiella tarda | Edwardsiellosis |
| Pseudomonas sp. | Bacterial hemorrhagic septicemia |
| Pasturella sp. | Pasteurellosis |
| Cytophaga and others | Fin rot |
| Sporocytophaga sp. | Salt water columnaris |
| Mycobacterium sp. | Mycobacteriosis |
| Norcardia asteroides | Nocardiosis |
| Streptomyces sp. | Streptomycosis |
| Streptococcus sp. | Streptococcosis |
| Eubacterium tarentellus | Eubacterial meningitis-- |

Column 9, line 22, after "mutant" should read --strain of the invention and the vaccine may be employed in substantially the same manner as described above for the live vaccine. The invention is described in further detail in the following non-limiting examples.--;

line 33, "S rensen" should read --Sørensen--;
line 39, "S rensen" should read --Sørensen--; and
line 41, "S rensen" should read --Sørensen--.

UNITED STATES PATENT AND TRADEMARK OFFICE
CERTIFICATE OF CORRECTION

PATENT NO. : 5,284,653
DATED : February 8, 1994
INVENTOR(S) : Wolf-Watz et al.

It is certified that error appears in the above-identified patent and that said Letters Patent is hereby corrected as shown below:

Column 11, line 40, "ColEi" should read --ColE1--.

Columns 13 and 14, "TABLE 4" and "TABLE 5" should be realigned so that they do not overlap.

Column 13, line 55, "#/1" should read --#/--.

Column 15, line 46, "anguillarym" should read --anguillarum--; and
line 52, "bvibriosis." should read --vibriosis--.

Column 16, line 12, *typhy* should read --*typhi*--.

Signed and Sealed this

Sixteenth Day of May, 1995

Attest:

Attesting Officer

BRUCE LEHMAN

Commissioner of Patents and Trademarks